(12) United States Patent
Bengtson et al.

(10) Patent No.: US 8,585,683 B2
(45) Date of Patent: Nov. 19, 2013

(54) ASSEMBLIES, SYSTEMS, AND METHODS FOR VACUUM ASSISTED INTERNAL DRAINAGE DURING WOUND HEALING

(75) Inventors: Bradley P Bengtson, Grand Rapids, MI (US); Patricia A McGuire, Ladue, MO (US)

(73) Assignee: KCI Medical Resources, Grand Cayman (KY)

( * ) Notice: Subject to any disclaimer, the term of this patent is extended or adjusted under 35 U.S.C. 154(b) by 304 days.

(21) Appl. No.: 12/661,293

(22) Filed: Mar. 15, 2010

(65) Prior Publication Data

US 2010/0179516 A1 Jul. 15, 2010

Related U.S. Application Data

(63) Continuation of application No. 11/810,027, filed on Jun. 4, 2007, now Pat. No. 7,699,831, which is a continuation-in-part of application No. 11/646,918, filed on Dec. 28, 2006.

(60) Provisional application No. 60/810,733, filed on Jun. 2, 2006.

(51) Int. Cl.
*A61M 1/00* (2006.01)
*A61M 27/00* (2006.01)

(52) U.S. Cl.
USPC .................... 604/541; 604/543; 604/540

(58) Field of Classification Search
USPC ........................... 604/313, 315, 541
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,969,057 A | 1/1961 | Simmons |
| 3,066,672 A | 12/1962 | Crosby, Jr. et al. |
| 3,367,332 A | 2/1968 | Groves |
| 3,394,702 A | 7/1968 | Heimlich et al. |
| 3,520,300 A | 7/1970 | Flower, Jr. |
| 3,556,101 A | 1/1971 | Economou |
| 3,568,675 A | 3/1971 | Harvey |
| 3,589,368 A | 6/1971 | Jackson |
| 3,595,241 A | 7/1971 | Sheridan |
| 3,648,692 A | 3/1972 | Wheeler |

(Continued)

FOREIGN PATENT DOCUMENTS

| | | |
|---|---|---|
| AU | 550575 A1 | 8/1982 |
| AU | 755496 | 2/2002 |

(Continued)

OTHER PUBLICATIONS

Product description Endo Sponge, www.bbraun.com, Jun. 18, 2008.

(Continued)

*Primary Examiner* — Susan Su
(74) *Attorney, Agent, or Firm* — Thomas J. Engellenner; Reza Moilaaghababa; Pepper Hamilton LLP

(57) ABSTRACT

Assemblies, systems, and methods convey fluid from an internal wound site or body cavity by applying negative pressure from a source outside the internal wound site or body cavity through a wound drain assembly that is placed directly inside the internal wound site or body cavity.

26 Claims, 7 Drawing Sheets

(56) References Cited

U.S. PATENT DOCUMENTS

| | | | |
|---|---|---|---|
| 3,682,180 A | 8/1972 | McFarlane | |
| 3,826,254 A | 7/1974 | Mellor | |
| 3,830,238 A | 8/1974 | Kurtz et al. | |
| 3,935,863 A | 2/1976 | Kliger | |
| 3,957,054 A | 5/1976 | McFarlane | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,217,904 A | 8/1980 | Zahorsky | |
| 4,233,969 A | 11/1980 | Lock et al. | |
| 4,245,630 A | 1/1981 | Lloyd et al. | |
| 4,250,882 A | 2/1981 | Adair | |
| 4,256,109 A | 3/1981 | Nichols | |
| 4,257,422 A | 3/1981 | Duncan | |
| 4,261,363 A | 4/1981 | Russo | |
| 4,275,721 A | 6/1981 | Olson | |
| 4,284,079 A | 8/1981 | Adair | |
| 4,294,240 A | 10/1981 | Thill | |
| 4,297,995 A | 11/1981 | Golub | |
| 4,317,452 A | 3/1982 | Russo et al. | |
| 4,333,468 A | 6/1982 | Geist | |
| 4,341,212 A * | 7/1982 | Medwid | 604/148 |
| 4,346,711 A | 8/1982 | Agdanowski et al. | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,398,910 A | 8/1983 | Blake et al. | |
| 4,419,097 A | 12/1983 | Rowland | |
| 4,430,084 A | 2/1984 | Deaton | |
| 4,432,853 A | 2/1984 | Banks | |
| 4,445,897 A | 5/1984 | Ekbladh et al. | |
| 4,465,485 A | 8/1984 | Kashmer et al. | |
| 4,475,909 A | 10/1984 | Eisenberg | |
| 4,480,638 A | 11/1984 | Schmid | |
| 4,523,920 A | 6/1985 | Russo | |
| 4,525,166 A | 6/1985 | Leclerc | |
| 4,525,374 A | 6/1985 | Vaillancourt | |
| 4,533,356 A | 8/1985 | Bengmark et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,553,966 A | 11/1985 | Korteweg | |
| 4,569,348 A | 2/1986 | Hasslinger | |
| 4,579,555 A | 4/1986 | Russo | |
| 4,605,399 A | 8/1986 | Weston et al. | |
| 4,608,041 A | 8/1986 | Nielsen | |
| 4,633,865 A | 1/1987 | Hengstberger et al. | |
| 4,640,688 A | 2/1987 | Hauser | |
| D288,962 S | 3/1987 | Blake | |
| 4,655,754 A | 4/1987 | Richmond et al. | |
| 4,664,662 A | 5/1987 | Webster | |
| 4,692,153 A | 9/1987 | Berlin et al. | |
| 4,710,165 A | 12/1987 | McNeil et al. | |
| 4,717,379 A | 1/1988 | Elkholwe | |
| 4,728,642 A | 3/1988 | Pawelchak et al. | 514/57 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,815,468 A | 3/1989 | Annand | |
| 4,825,866 A | 5/1989 | Pierce | |
| 4,826,494 A | 5/1989 | Richmond et al. | |
| 4,838,883 A | 6/1989 | Matsuura | |
| 4,840,187 A | 6/1989 | Brazier | |
| 4,844,072 A | 7/1989 | French et al. | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,899,965 A | 2/1990 | Usui | |
| 4,906,233 A | 3/1990 | Moriuchi et al. | |
| 4,906,240 A | 3/1990 | Reed et al. | |
| 4,908,350 A | 3/1990 | Kramer et al. | |
| 4,919,654 A | 4/1990 | Kalt et al. | |
| 4,925,452 A | 5/1990 | Melinyshyn et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,045,075 A | 9/1991 | Ersek | |
| 5,053,021 A | 10/1991 | Feibus | |
| 5,085,633 A | 2/1992 | Hanifl et al. | |
| 5,086,170 A | 2/1992 | Luheshi et al. | |
| 5,092,858 A | 3/1992 | Benson et al. | |
| 5,100,395 A | 3/1992 | Rosenberg | |
| 5,100,396 A | 3/1992 | Zamierowski | |
| 5,116,310 A | 5/1992 | Seder et al. | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,180,375 A | 1/1993 | Feibus | |
| 5,192,266 A | 3/1993 | Wilk | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,492 A | 10/1994 | Feibus | |
| 5,358,494 A | 10/1994 | Svedman | |
| 5,360,414 A | 11/1994 | Yarger | |
| 5,437,622 A | 8/1995 | Carion | |
| 5,437,651 A | 8/1995 | Todd et al. | |
| 5,437,683 A | 8/1995 | Neumann et al. | |
| 5,441,481 A | 8/1995 | Mishra et al. | |
| 5,443,848 A | 8/1995 | Kramer et al. | |
| 5,451,204 A | 9/1995 | Yoon | |
| 5,466,231 A | 11/1995 | Cercone et al. | 604/369 |
| 5,484,399 A | 1/1996 | Diresta et al. | |
| 5,484,428 A | 1/1996 | Drainvill et al. | |
| 5,527,293 A | 6/1996 | Zamierowski | |
| 5,549,579 A | 8/1996 | Batdorf et al. | |
| 5,549,584 A | 8/1996 | Gross | |
| 5,554,138 A | 9/1996 | Stanford et al. | |
| 5,556,375 A | 9/1996 | Ewall | |
| 5,599,330 A | 2/1997 | Rainin | |
| 5,607,388 A | 3/1997 | Ewall | |
| 5,628,735 A | 5/1997 | Skow | |
| 5,636,643 A | 6/1997 | Argenta et al. | |
| 5,637,103 A | 6/1997 | Kerwin et al. | |
| 5,645,081 A | 7/1997 | Argenta et al. | |
| 5,662,598 A | 9/1997 | Tobin | |
| 5,678,564 A | 10/1997 | Lawrence et al. | |
| 5,701,917 A | 12/1997 | Khouri | |
| 5,792,173 A | 8/1998 | Breen et al. | |
| 5,891,111 A | 4/1999 | Ismael | |
| 5,893,368 A | 4/1999 | Sugerman | |
| 5,902,260 A | 5/1999 | Gilman et al. | |
| 5,911,222 A | 6/1999 | Lawrence et al. | |
| 5,921,972 A | 7/1999 | Skow | |
| 5,938,626 A | 8/1999 | Sugerman | |
| 5,947,953 A | 9/1999 | Ash et al. | |
| 6,042,539 A | 3/2000 | Harper et al. | |
| 6,051,747 A | 4/2000 | Lindqvist et al. | |
| 6,071,267 A | 6/2000 | Zamierowski | |
| 6,099,513 A | 8/2000 | Spehalski | |
| 6,135,116 A | 10/2000 | Vogel et al. | |
| 6,174,306 B1 | 1/2001 | Fleischmann | |
| 6,190,349 B1 | 2/2001 | Ash et al. | |
| 6,235,009 B1 | 5/2001 | Skow | |
| 6,241,747 B1 | 6/2001 | Ruff | |
| 6,264,979 B1 | 7/2001 | Svedman | |
| 6,287,316 B1 | 9/2001 | Agarwal et al. | |
| 6,290,685 B1 | 9/2001 | Insley et al. | |
| 6,345,623 B1 | 2/2002 | Heaton et al. | |
| 6,383,162 B1 | 5/2002 | Sugarbaker | |

(56) References Cited

U.S. PATENT DOCUMENTS

| | | | |
|---|---|---|---|
| 6,458,109 B1 | 10/2002 | Henley et al. | |
| 6,478,789 B1 | 11/2002 | Spehalski et al. | |
| 6,488,643 B1 | 12/2002 | Tumey et al. | |
| 6,493,568 B1 | 12/2002 | Bell et al. | |
| 6,537,241 B1 | 3/2003 | Odland | |
| 6,553,998 B2 | 4/2003 | Heaton et al. | |
| 6,565,544 B1 | 5/2003 | Rainin | |
| 6,605,068 B2 | 8/2003 | Righetti | |
| 6,626,891 B2 | 9/2003 | Ohmstede | |
| 6,685,681 B2 | 2/2004 | Lockwood et al. | |
| 6,695,823 B1 | 2/2004 | Line et al. | |
| 6,752,794 B2 | 6/2004 | Lockwood et al. | |
| 6,814,079 B2 | 11/2004 | Heaton et al. | |
| 6,855,135 B2 | 2/2005 | Lockwood et al. | |
| 6,866,657 B2 | 3/2005 | Shchervinsky | |
| 6,913,589 B2 | 7/2005 | Dextradeur et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,105,001 B2 | 9/2006 | Mandelbaum | |
| 7,182,758 B2 | 2/2007 | McCraw | |
| 7,195,624 B2 | 3/2007 | Lockwood et al. | |
| 7,276,051 B1 | 10/2007 | Henley et al. | |
| 7,322,971 B2 | 1/2008 | Shehada | |
| 7,338,482 B2 | 3/2008 | Lockwood et al. | |
| 7,381,859 B2 | 6/2008 | Hunt et al. | 602/46 |
| 7,413,571 B2 | 8/2008 | Zamierowski | |
| 7,476,205 B2 | 1/2009 | Erdmann | |
| 7,658,735 B2 | 2/2010 | Spehalski | |
| 7,717,871 B2 | 5/2010 | Odland | |
| 7,918,817 B2 | 4/2011 | Schon et al. | |
| 2001/0029956 A1 | 10/2001 | Argenta | |
| 2001/0043943 A1 | 11/2001 | Coffey | |
| 2002/0062097 A1 | 5/2002 | Simpson | |
| 2002/0065494 A1 | 5/2002 | Lockwood et al. | |
| 2002/0077661 A1 | 6/2002 | Saadat | |
| 2002/0115951 A1 | 8/2002 | Norstrem et al. | |
| 2002/0115956 A1 | 8/2002 | Ross | |
| 2002/0120185 A1 | 8/2002 | Johnson | |
| 2002/0128578 A1 | 9/2002 | Johnston et al. | |
| 2002/0143286 A1 | 10/2002 | Tumey | |
| 2002/0161317 A1 | 10/2002 | Risk et al. | |
| 2003/0109855 A1 | 6/2003 | Solem et al. | |
| 2003/0208149 A1 | 11/2003 | Coffey | |
| 2004/0260230 A1 | 12/2004 | Randolph | |
| 2005/0004536 A1 | 1/2005 | Opie et al. | |
| 2005/0085795 A1 | 4/2005 | Lockwood | |
| 2005/0101922 A1 | 5/2005 | Anderson et al. | |
| 2005/0131327 A1 | 6/2005 | Lockwood et al. | |
| 2005/0137539 A1* | 6/2005 | Biggie et al. | 604/313 |
| 2005/0148963 A1* | 7/2005 | Brennan | 604/364 |
| 2005/0261642 A1 | 11/2005 | Weston | |
| 2005/0273066 A1 | 12/2005 | Wittmann | |
| 2006/0015087 A1 | 1/2006 | Risk et al. | |
| 2006/0029650 A1 | 2/2006 | Coffey | |
| 2006/0041247 A1 | 2/2006 | Petrosenko et al. | |
| 2006/0079852 A1 | 4/2006 | Bubb | |
| 2006/0189910 A1 | 8/2006 | Johnson et al. | |
| 2007/0027414 A1 | 2/2007 | Hoffman et al. | |
| 2008/0058684 A1 | 3/2008 | Ugander et al. | |
| 2008/0167593 A1 | 7/2008 | Fleischmann | |
| 2009/0099519 A1 | 4/2009 | Kaplan | |
| 2010/0030132 A1 | 2/2010 | Niezgoda et al. | |

FOREIGN PATENT DOCUMENTS

| | | |
|---|---|---|
| CA | 2005436 | 6/1990 |
| CA | 2 303 085 | 3/1999 |
| DE | 26 40 413 A1 | 3/1978 |
| DE | 2754775 A1 | 6/1979 |
| DE | 43 06 478 A1 | 9/1994 |
| DE | 295 04 378 U1 | 10/1995 |
| DE | 20115990 U1 | 12/2001 |
| DE | 69806842 T2 | 1/2003 |
| DE | 60118546 T2 | 8/2006 |
| DE | 102006032870 | 1/2008 |
| EP | 0100148 A1 | 2/1984 |
| EP | 0117632 A2 | 9/1984 |
| EP | 0161865 A2 | 11/1985 |
| EP | 271491 B1 | 6/1988 |
| EP | 0358302 A2 | 3/1990 |
| EP | 0506992 | 10/1992 |
| EP | 0555293 | 8/1993 |
| EP | 0777504 | 6/1997 |
| EP | 0 853 950 B1 | 10/2002 |
| EP | 1284777 | 2/2003 |
| EP | 1 088 569 B1 | 8/2003 |
| EP | 1018967 B1 | 8/2004 |
| EP | 0 688 189 B2 | 6/2005 |
| EP | 0 620 720 B2 | 11/2006 |
| GB | 692578 | 6/1953 |
| GB | 2058227 A | 4/1981 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2329127 A | 3/1999 |
| GB | 2 333 965 A | 8/1999 |
| GB | 2342584 A | 4/2000 |
| GB | 2 329 127 B | 8/2000 |
| GB | 2365350 A | 2/2002 |
| JP | 3056429 U | 5/1991 |
| JP | H3-56429 | 5/1991 |
| JP | 4129536 | 4/1992 |
| SG | 71559 | 4/2002 |
| WO | WO 80/02182 | 10/1980 |
| WO | WO 87/01027 A1 | 2/1987 |
| WO | WO 87/04626 | 8/1987 |
| WO | WO 90/10424 | 9/1990 |
| WO | WO 92/07519 A1 | 5/1992 |
| WO | WO 93/09727 | 5/1993 |
| WO | WO 94/20041 | 9/1994 |
| WO | WO 96/05873 | 2/1996 |
| WO | WO 96/34636 A | 11/1996 |
| WO | WO 97/18007 | 5/1997 |
| WO | WO-99/01173 A1 | 1/1999 |
| WO | WO 99/13793 | 3/1999 |
| WO | WO 00/07653 | 2/2000 |
| WO | WO 00/07653 A1 | 2/2000 |
| WO | WO 00/42958 A1 | 7/2000 |
| WO | WO 00/57794 A1 | 10/2000 |
| WO | WO 00/59418 A1 | 10/2000 |
| WO | WO 00/59424 A1 | 10/2000 |
| WO | WO 01/34223 A1 | 5/2001 |
| WO | WO 01/71231 A1 | 9/2001 |
| WO | WO01/85248 | 11/2001 |
| WO | WO 01/85248 A | 11/2001 |
| WO | WO 01/89431 A1 | 11/2001 |
| WO | WO 03/057307 A1 | 7/2003 |
| WO | WO 03/086232 A2 | 10/2003 |
| WO | WO2004/041346 | 5/2004 |
| WO | WO 2006/048246 A1 | 5/2006 |
| WO | WO 2007/031762 A | 3/2007 |
| WO | WO 2007/041642 A | 4/2007 |
| WO | WO 2007/109209 A2 | 9/2007 |
| WO | WO 2007/133618 A2 | 11/2007 |
| WO | WO 2008/014358 A2 | 1/2008 |
| WO | WO 2008/040020 A | 4/2008 |
| WO | WO 2008/041926 A1 | 4/2008 |
| WO | WO 2008/103625 A2 | 8/2008 |
| WO | WO 2012/080783 | 6/2012 |

OTHER PUBLICATIONS

Mees et al., "Endo-Vacuum Assisted Closure Treatment for Rectal Anastomotic Insufficiency", Diseases of Colon and Rectum, vol. 51: 404-410, 2008.

Cholmondeley Williams et al., "The Effect of Hematoma on the Thickness of Pseudosheaths Around Silicone Implants", presented at the Am Soc of Plastic and Reconstructure Surgeons, Houston, TX, Oct. 30, 1974.

(56) References Cited

OTHER PUBLICATIONS

Shermak, Michele A et al., "Seroma Development Following Body Contouring Surgery for Massive Weight Loss: Patient Risk Factors and Treatment Strategies", Division of Plastic Surgery and the Department of Surgery, the Johns Hopkins Medical Inst5itutions, pp. 280-288; Jul. 12, 2007.
Saxena et al., "Vacuum-Assisted Closure: Microdeformations of Wounds and Cell Proliferation", Plastic and Reconstructive Surgery, J vol. 115, No. 5, pp. 1086-1096, Oct. 2004.
Response filed Oct. 4, 2010 for U.S. Appl. No. 12/466,973.
Advisory Action date mailed Oct. 12, 2010 for U.S. Appl. No. 12/466,973.
RCE/Response filed Nov. 2, 2010 for U.S. Appl. No. 12/466,973.
N.A. Badautdihov, "Variant of External . . . ", edited by V. Ye Volkov et al. (Chuvashia State University, Cheboksary, U.S.S.R. 1986);pp. 94-96.
Louis C. Argenta, MD and Michael J. Morykwas, PhD; "Vacuum-Assisted Closure: A New Method for Wound . . . ": Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al., "Negative-Pressure Dressings as a Bolster for Skin Grafts"; Annals of Plastic Surgery, vol. 40, No. 5, May 1998, pp. 453-457.
John Masters; "Reliable . . . "; Letter to the Editor, British Journal of Plastic Surgery, 1998, vol. 51 (3), p. 267; Elsevier Science/British Assocn of Plastic Surgeons, UK.
S.E. Greer, et al, "The Use of Subatmospheric Pressure Dressing Therapy to Close Lymphocutaneous Fistulas of . . . ", British Journal of Plastic Suraery (2000), 53, pp. 484-487.
George V. Letsou, MD., et al.; "Stimulation of Adenylate Cyclase Activity in Cultured Endothelial Cells . . . "; Journal of Cardiovascular Surgery, 31, 1990, pp. 634-639.
Orringer, Jay, et al. "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opionion; PCT International Application PCT/GB98/02713; Jun. 8, 1999.
PCT International Examination and Search Report; PCT International Application PCT/GB96/02802; Jan. 15, 1998 & Apr. 29, 1997.
PCT Written Opinion, PCT International Application PCT/GB96/02802; Sep. 3, 1997.
Dattilo, Philip, P., Jr., et al., "Medical Textiles: Application of an . . . "; Journal of Textile and Apparel, Technology and Management, vol. 2, Issue 2, Spring 2002, pp. 1-5.
Kostyuchenok, B.M., et al., "Vacuum Treatment in the Surgical Managment of . . . ", Vestnik Khirurgi, Sep. 1986, pp. 18-21 and 6 page English translation thereof.
Davydov, Yu. A., et al., "Vacuum Therapy in the Treatment of Purulent Lactation . . . "; Vestnik Khirurgi, May 14, 1986, pp. 66-70, and 9 page English translation thereof.
Yusupov, Yu, N. et al., "Active Wound Drainage", Vestnik Khirurgi, vol. 138, Issue 4, 1987, and 7 page English translation thereof.
Davydov, Yu. A. et al., "Bacteriological and Cytological Assessment of Vacuum Therapy for . . . "; Vestnik Khirurgi, Oct. 1988, pp. 48-52, and 8 page English translation thereof.
Davydov, Yu. A. et al, Concepts for the Clinical-Biological Management of the Wound . . . ; Vestnik Khirurgi, Jul. 7, 1980, pp. 132-136, and 8 page English translation thereof.
Chariker, Mark E. M.D., et al., "Effective Management of Incisional and Cutaneous Fistulae with Closed Suction . . . "; Contemporary Surgery, vol. 34, Jun. 1989, pp. 59-63.
Egnell Minor, "Instruction Book", First Edition, 300 7502, Feb. 1975, pp. 24.
Egnell Minor, "Addition to the Users Manual Concerning Overflow Protection—Concerns All Egnell Pumps", Feb. 3, 1983, pp. 2.
Svedman, P., "Irrigation Treatment of Leg Ulcers", The Lancet, Sep. 3, 1983, pp. 532-534.
Chinn, Steven D. et al., "Closed Wound Suction Drainage", The Journal of Foot Surgery, vol. 4, No. 1, 1985, pp. 76-81.
Arnljots, Bjorn et al., "Irrigation Treatment in Split-Thickness Skin Grafting of Intractable . . . ", Scand J. Plastic Reconstr. Surgery, No. 19, 1985, pp. 211-213.
Svedman, P., "A Dressing Allowing Continuous Treatment . . . ", IRCS Medical Science: Biomedical Technoloay, Clinical Medicine, Surgery and Transplantation, vol. 7, 1979, p. 221.
Svedman, P. et al., "A Dressing System Providing Fluid Supply and Suction Drainage Used for . . . ", Annals of Plastic Surgery, vol. 17, No. 2, Aug. 1986, pp. 125-133.
K.F. Jeter, T.E. Tintle, and M. Chariker, "Managing . . . ", Chronic Wound Care, edited by D. Krasner (Health Managment Publications, Inc., King of Prussia, PA 1990), pp. 240-246.
G. Zivadinovic, V. Dukic, Z. Maksimovic, D. Radak, and P. Peska, "Vacuum Therapy in the . . . ", Timok Medical Journal 11 (1986), pp. 161-164.
F.E. Johnson, "An Improved Technique for Skin Graft Placement Using a Suction Drain", Surgery, Gynecology, and Obstetrics 159 (1984), pp. 584-585.
A.A. Safronov, Dissertation Abstract . . . , (Central Scientific Research Institute of Traumatology and Orthopedics, Moscow, U.S.S.R. 1967).
M. Schein, R. Saadia, J.R. Jamieson, and G.A G. Decker, "The 'Sandwich Technique' in the Management of the Open Abdomen", British Journal of Surgery 73 (1936), pp. 369-370.
D.E. Tribble, "An improved Sump Drain-Irrigation Device of Simple Construction", Archives of Surgery 105 (1972), pp. 511-513.
M.J. Morykwas, L.C. Argenta, E.I. Shelton-Brown, and W. McGuirt, "Vacuum-Assisted Closure: A New Method . . . ", Annals of Plastic Surgery 38 (1997), pp. 553-562 (Morykwas I).
C. E. Tennants, "The Use of Hypermia in the Postoperative Treatment of Lesions of the Extremeties . . . ", Journal of the American Medical Association 64 (1915), pp. 1548-1549.
Selections from W. Meyer and V. Schmieden, Bier's Hyperemic Treatment in . . . , (W.B. Saunders Co., Philadelphia, PA 1909), pp. 17-25, 44-64, 90-96, 167-170, and 210-211.
The V.A.C.™ Vacuum Assisted Closure, Assisting in Wound Closure, Brochure, Jan. 1996, 5 pages, 1-A-042, KCI®, San Antonio, Texas.
Argenta et al., "The V.A.C.™, Case Study #4", Case Study, Mar. 1995, 1 page, 35-D-004, KCI®, San Antonio, Texas.
Argenta et al., "The V.A.C.™, Case Study #3", Case Study, Mar. 1995, 1 page, 35-D-003, KCI®, San Antonio, Texas.
"The V.A.C.® Operations Summary, the V.A.C.® Wound Closure System Applications", Brochure, Mar. 1997, 4 pages, 1-A-060, KCI®, San Antonio, Texas.
"The V.A.C.® Operations Summary, The V.A.C.® Wound Closure System Applications", Brochure, Mar. 1999, 2 pages, 1-A-060, KCI®, San Antonio, Texas.
Argenta et al., "V.A.C.® Wound Closure Device Case Study #3", Case Study, Apr. 1998, 1 page, 35-D-003, KCI®, San Antonio, Texas.
Argenta et al., "V.A.C.® Wound Closure Device Case Study #1", Case Study, Apr. 1998, 1 page, 35-D-001, KCI®, San Antonio, Texas.
Argenta et al., "V.A.C.® Wound Closure Device Case Study #8", Case Study, Jun. 1996, 2 pages, 35-D-008, KCI®, San Antonio, Texas.
Argenta et al., "V.A.C.® Wound Closure Device Case Study #7", Case Study, Jun. 1996, 2 pages, 35-D-007, KCI®, San Antonio, Texas.
Argenta et al., "V.A.C.® Wound Closure Device Case Study #6", Case Study, Jun. 1996, 2 pages, 35-D-006, KCI®, San Antonio, Texas.
Argenta et al., "V.A.C.® Wound Closure Device Case Study #9", Case Study, Jun. 1996, 2 pages, 35-D-009, KCI®, San Antonio, Texas.
Argenta et al., "V.A.C.® Wound Closure Device Case Study #5". Case Study, Aug. 1994, 2 pages, 35-D-005, KCI®, San Antonio, Texas.

(56) References Cited

OTHER PUBLICATIONS

Argenta et al., "V.A.C.® Wound Closure Device Case Study #4", Case Study, Aug. 1994, 2 pages, 35-D-004, KCI®, San Antonio, Texas.
Argenta et al., "V.A.C.® Wound Closure Device Case Study #3", Case Study, Aug. 1994, 2 pages, 35-D-003, KCI®, San Antonio, Texas.
Argenta et al., "V.A.C.® Wound Closure Device Case Study #2", Case Study, Aug. 1994, 2 pages, 35-D-002, KCI®, San Antonio, Texas.
Argenta et al., "V.A.C.® Wound Closure Device Case Study #1", Case Study, Aug. 1994, 2 pages, 35-D-001, KCI®, San Antonio, Texas.
Ex parte Quayle Office Action dated Feb. 7, 2005 for U.S. Appl. No. 10/275,671.
Amendment filed Apr. 8, 2005 to Office Action dated Feb. 7, 2005 for U.S. Appl. No. 10/275,671.
Non-Final Office Action dated Jun. 27, 2005 for U.S. Appl. No. 10/275,671.
Response filed Oct. 19, 2005 to Non-Final Office Action dated Jun. 27, 2005 for U.S. Appl. No. 10/275,671.
Non-Final Office Action dated Jan. 10, 2006 for U.S. Appl. No. 10/275,671.
Response filed Jul. 10, 2006 to Non-Final Office Action dated Jan. 10, 2006 for U.S. Appl. No. 10/275,671.
Supplemental Amendment filed Aug. 10, 2006 for U.S. Appl. No. 10/275,671.
Final Office Action dated Apr. 17, 2007 for U.S. Appl. No. 10/275,671.
Response filed Jun. 12, 2007 to Final Office Action dated Apr. 17, 2007 for U.S. Appl. No. 10/275,671.
Advisory Action dated Jul. 11, 2007 for U.S. Appl. No. 10/275,671.
Response filed Aug. 17, 2007 to Advisory Action dated Jul. 11, 2007 for U.S. Appl. No. 10/275,671.
Non-Finai Office Action dated Sep. 5, 2007 for U.S. Appl. No. 10/275,671.
Response filed Sep. 5, 2007 to Non-Final Office Action dated Sep. 5, 2007 for U.S. Appl. No. 10/275,671.
Notice of Allowance and Fee(s) Due dated Feb. 4, 2008 for U.S. Appl. No. 10/275,671.
V.A. Solovev et al., "Guidelines, The Method . . . ", editor-in-chief Prov. V.I. Parahonyak (S.M. Kirov Gorky State Medical Institute, Gorky, U.S.S.R. 1987) ("Solovey Guidelines".
V.A. Kuznetsov & N.A. Bagautdinov, "Vacuum and Vacuum-Sorption . . . ", edited by B.M, Kostyuchenok et al, (Moscow, U.S.S.R. Oct. 28-29, 1936) pp. 91-92 ("Bagautdinov II").
V.A. Solovev, Dissertation Abstract, Treatment and Prevention of Suture Failures . . . , (S.M. Kirov Gorky State Medical Institute, Gorky, U.S.S.R. 1988) ("Solovev Abstract").
Notice of Allowance date mailed Feb. 4, 2008 for U.S. Appl. No. 10/275,671.
Translation of the Nullity Action of Sep. 10, 2010 (submitted by applicant).
Meyer et al., "A New Abdominal Drain for Overflowing Lavage in Instances of Severe Pancreatitis with Persistent . . . ", Surg. Gynecol. Obstet. Sep. 1987: 165 (3): 271-3.
Poritz, "Percutaneous Drainage and Ileocolectomy for Spontaneous Intraabdominal Abscess in Chrohns Disease . . . ", J, Gastrointest. Surg. Feb. 2007: 11 (2):204-0.
Khurrum et al., "Percutaneous Postoperative Intra-abdominal Abscess Drainage After Elective Colorectal Surgery . . . ", Tech. Coloprotocl. Dec. 2002: 6(3): 159-64.
Reckard et al., "Management of Intraabdominal . . . ", Journal of Vascual Interventional Journal of Vascual Interventional Radiology, vol. 16, Issue 7, pp. 1019-1021.
Latenser et al., "A Pilot Study Comparing Percutaneous Decompression with Decompressive Laparotomy for Acute . . . ", J Burn Care & Rehav, 23(3): 190-195.
Kubiak et al., "Reduced Intra-Peritoneal Inflammation . . . ", Critical Care I, vol. 207, No. 3S, Sep 2008, S34-35.
Kaplan, "Managing the Open Abdomen"; Ostomy Wound Management, Jan. 2004; 50 1A supply; C2; 1-8.
Kaplan et al., "Guidelines for the Management of the Open Abdomen", Wounds Oct. 2005; 17 (Suppl 1); S1S24.
Garner et al., "Vacuum-assisted Wound Closure Provides Early Fascial Reapproximation . . . ", The American Journal of Surgery, Dec. 2001; 182 (6); 630-8.
Barker et al., "Vacuum Pack of Technique of Temporary Abdominal Closure: A 7-year Experience with 112 Patients . . . ", J Trauma Feb. 1, 2000; 48 (2): 201-6.
Brock et al., "Temporary Closure of Open Abdominal Wounds: The Vacuum Pack", Am Surg. Jan. 1995, 61 (1): 30-5.
Sherck et al., "Covering the 'Open Abdomen': A Better Technique", Am Surg. Sep. 1998: 64(9): 854-7.
Dubick et al., "Issues of Concern Regarding the Use of Hypertonic/Hyperoncotic Fluid Resuscitation of Hemorrhagic Hypotension . . . ", Apr. 2006; 25 (4); 321-8.
Burdette, "Systemic Inflammatory Response Syndrome", http://emedicine.medscape.com/article/168943-print, Apr. 2007.
Beamis Hydrophobic Rigid Canisters—http://www.bemishealthcare.com/docs/Canister Hydrophobic.pdf (date unknown).
Fink et al., "Textbook of Critical Care", 5th ed. (Philadelphia: Elsevier, 2005), 1933-1943.
International Search Report and Written Opinion date mailed Nov. 5, 2009 for PCT/US2009/044264.
International Search Report and Written Opinion date mailed Nov. 18, 2009 for PCT/US2009/044230.
International Search Report and Written Opinion date mailed Sep. 17, 2009 for PCT/US2009/044240.
International Search Report and Written Opinion date mailed Nov. 5, 2009 for PCT/US2009/044268.
International Search Report and Written Opinion date mailed Oct. 6, 2009 for PCT/US2009/044226.
International Search Report and Written Opinion date mailed Oct. 15, 2009 for PCT/US2009/044244.
International Search Report and Written Opinion date mailed Oct. 6, 2009 for PCT/US2009/044266.
International Search Report and Written Opinion date mailed Nov. 5, 2009 for PCT/US2009/044245.
International Search Report and Written Opinion date mailed Oct. 23, 2009 for PCT/US2009/044235.
Restriction Requirement date mailed Jan. 4, 2010 for U.S. Appl. No. 12/466,973.
Response filed Jan. 21, 2010 for U.S. Appl. No. 12/466,973.
Non-Final Office Action date mailed Mar. 5, 2010 for U.S. Appl. No. 12/466,973.
Response filed May 20, 2010 for U.S. Appl. No. 12/466,973.
Examiner Interview Summary date mailed May 25, 2010 for U.S. Appl. No. 12/466,973.
Final Office Action date mailed Aug. 12, 2010 for U.S. Appl. No. 12/466,973.
US 6,216,701, 04/2001, Heaton (withdrawn)

\* cited by examiner

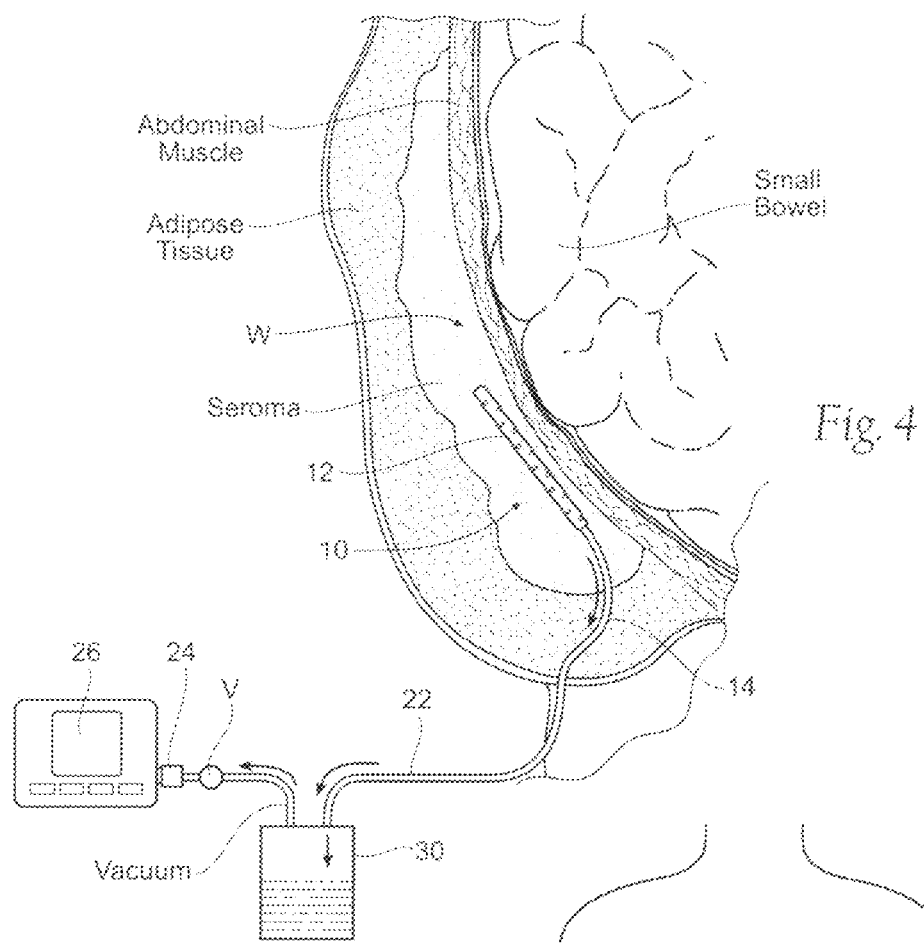
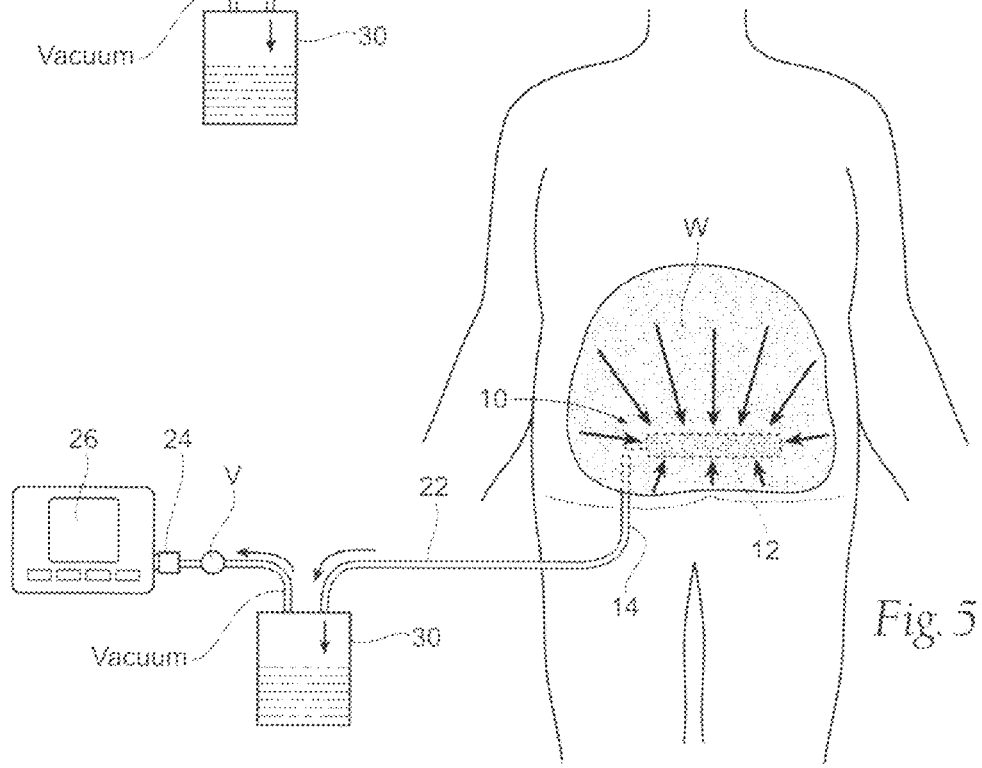
Fig. 4
Fig. 5

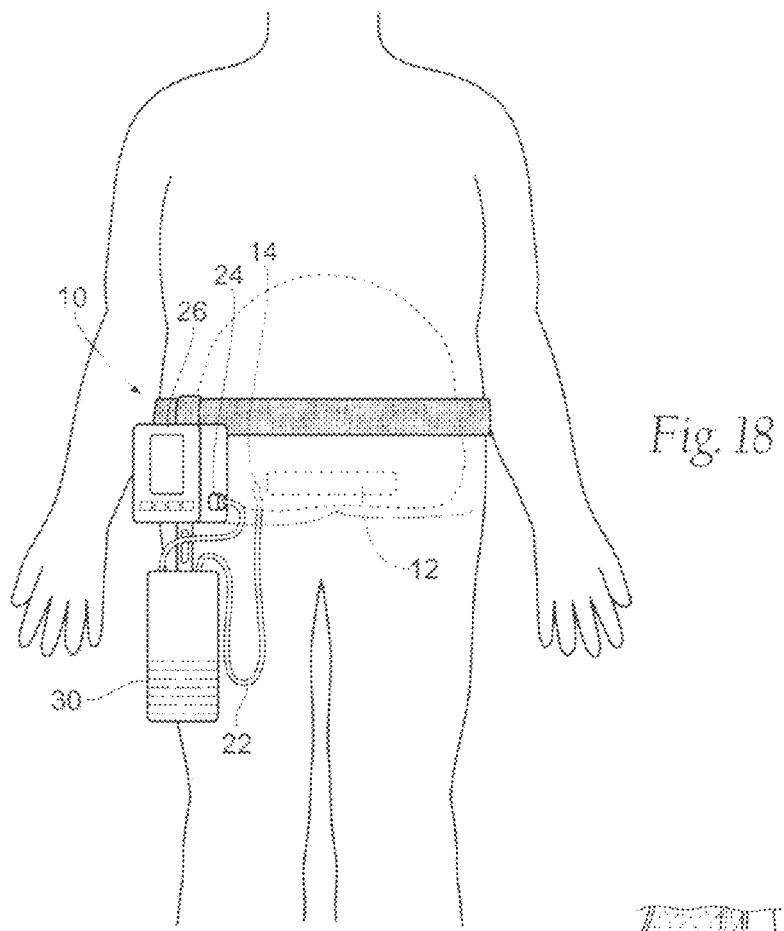
Fig. 18
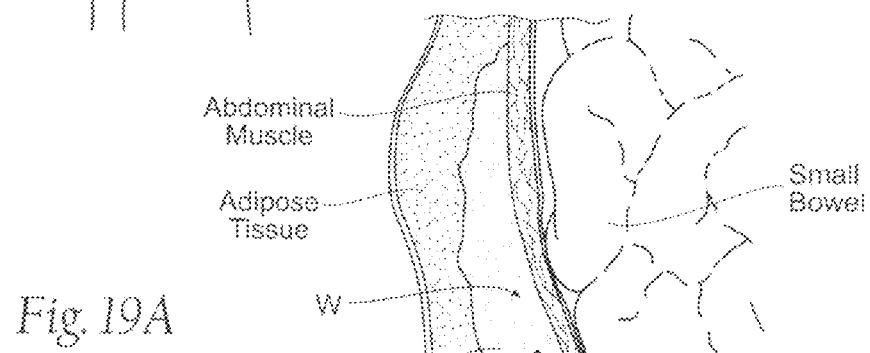
Fig. 19A
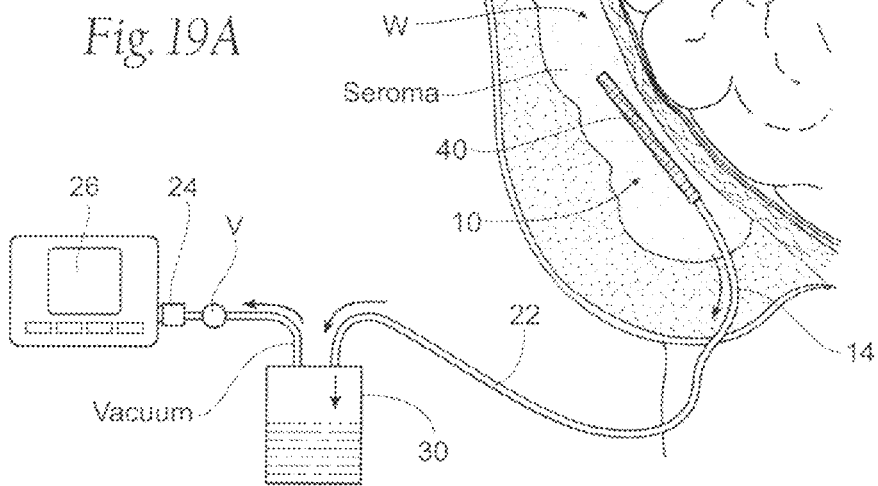

ASSEMBLIES, SYSTEMS, AND METHODS FOR VACUUM ASSISTED INTERNAL DRAINAGE DURING WOUND HEALING

RELATED APPLICATION

This application is a continuation of application Ser. No. 11/810,027 filed 4 Jun. 2007 now U.S. Pat. No. 7,699,831, which is a continuation-in-part of application Ser. No. 11/646,918, filed Dec. 28, 2006 and entitled Assemblies, Systems, and Methods for Vacuum Assisted Internal Drainage During Wound Healing, which claims the benefit of U.S. Provisional Patent Application Ser. No. 60/810,733, filed Jun. 2, 2006, and entitled "Foam Sponge Vacuum Assisted Internal Drainage System," which are each incorporated herein by reference.

FIELD OF THE INVENTION

This application relates generally to the drainage of fluid from the body during the wound healing process, e.g., following surgery, trauma, or placement of implants or surgical devices.

BACKGROUND OF THE INVENTION

During surgery, or as a result of trauma, tissue volume can be removed or altered, and an open or dead space is created within the tissue that was previously attached to other tissue. The very small blood vessels that previously ran from the underlying tissue (i.e., muscle, connective tissue) to the overlying tissue (i.e., skin, muscle) can be cut or damaged. Although these vessels usually do not cause significant blood loss, they do allow escape of blood serum into the area. Human blood serum contains about ninety-three percent water and about seven percent protein (mostly albumin).

Following surgery or due to trauma, there can also be resulting tissue damage, regardless of how careful the surgeon is. This tissue damage results in cellular death, and the body's natural defense reaction is an inflammatory one. Because of the inflammation, cell death, and increased vascular permeability, fluid can also accumulate in the operative space. The larger the operative space, the greater is the potential for internal fluid collection.

The body can resolve the accumulation of fluid over time, if there is some form of natural drainage, and if there is not continued irritation to the area, and if circulation to the area is sufficient, and if the person is in good health or the volume of fluid collection is itself not too large.

If, for whatever reason, the body is unable to itself efficiently absorb the excess fluid, a seroma can occur. A seroma is defined as a sterile accumulation of blood serum in a circumscribed tissue location or operative space. A seroma is not by definition an "infection;" it does not necessarily involve the presence of white blood cells, bacteria, and the breakdown products of both. A seroma is fluid and blood serum that has accumulated in a dead space in the tissue. A seroma is the result of tissue insult and the product of tissue inflammation and the body's defense mechanisms.

Seromas commonly develop following drain removal or when fluid is produced at a greater rate than it is absorbed. Conventional wound management techniques are commonly applied when a seroma becomes a clinical concern. Placement of a seroma catheter or additional drain, as well as repeated or serial drainage of a seroma, may be required. A seroma or fluid collection is by far the most common complication in surgery today. Such complications result in a significant amount of lost income to patients, as well as expenses to insurers and physicians who have to care for these patients that require serial drainage. Such complications also delay wound healing, may entail additional surgical procedures, and ultimately delay the patient's return to work and routine functional activity. Seroma management can also be costly and, further, can place health care workers to additional needle exposure risks and related outcomes such as hepatitis, etc.

The aim of wound management in both chronic and acute situations is to assist the natural process and prevent further complications such as infection, slough, necrosis formation, and chronic seroma cavities. Maintenance of the optimum wound healing environment is essential, ensuring the wound is kept moist and warm. Wound care products strive to achieve these results and, in turn, help to promote rapid wound closure.

Fluid drainage can be as simple as creating an opening at the lowest edge of the seroma, and keeping this open and clean to allow continued drainage. A clinically accepted way to deal with a seroma that does not appear to be resolving on its own, is to install a continuous drain system, coupled with treatment with antibiotics to prevent infection while the continuous drain system is in use. There are currently numerous types of wound drains on the market, most of them utilizing some form of tubing to withdraw fluid from the wound until the body can resorb the fluid without assistance. A continuous drain system allows the fluid to continuously escape until the body can complete the healing process on its own.

A representative prior art continuous drain system can comprise an implanted device such as a piece of rubber tubing (Penrose drain) (as shown in FIG. 1), which provides dependent gravity drainage or responds to a negative suction force generated by a manual closed suction bulb. These types of drains constitute the most common devices currently available. The problem with these devices is that, although they may drain fluid, fluid drainage is limited to fluid directly around the drain itself. As a result, current drains may manage fluid collection, but they do not effectively clear all of the fluid in the space and, more importantly, they do not clear enough fluid to effectively seal down and close off the dead space.

Another representative prior art continuous drain system, which is currently approved for external use only, can take the form of an externally applied device comprising a piece of foam with an open-cell structure, which coupled to one end of a drain tube (see FIG. 2). The foam is placed externally on top of the wound or skin, and the entire external area is then covered with a transparent adhesive membrane, which is firmly secured to the healthy skin around the wound margin. The opposite end of the drain tube is connected to a vacuum source, and blood or serous fluid are drawn from the wound through the foam into a reservoir for subsequent disposal. Among the numerous names this prior art system is called are "Vacuum Assisted Closure device" or VAC devices. Conventional VAC devices, however, are only approved and used for external wounds only. Conventional VAC devices are not approved or used for internal wounds or operative sites.

Current wound drain devices assemblies at times do not remove a substantial amount of fluid from within a wound and have other performance issues. For example, external VAC devices clear fluid directly around external wounds (as FIG. 3 shows), and they are limited to the application to external wounds only. They leave the remainder of the wound site or operating space open and filled with fluid.

Furthermore, the clinical use of external VAC devices may not make wound drainage more cost-effective, clinician-friendly, and patient-friendly.

For example, the foam structures and adhesive membranes associated with conventional practices of external VAC need to be periodically removed and replaced. Currently, dressing changes are recommended every 48 hours for adults with non-infected wounds, and daily for infants and adolescents. Current techniques place the foam material in direct contact with granulating tissue. Removal of the foam structures in the presence of granulating tissue and the force of pressure on the wound bed that this removal can cause pain or discomfort. The sponge can also break into particulates and remain in the wound. Furthermore, the multiple steps of the conventional external VAC procedure—removing the adhesive membrane, then removing the old foam structures, then inserting the new foam structures, and then reapplying the adhesive member along the entire periphery of the wound—are exacting, tedious and time consuming. They only prolong pain or discomfort, and cause further disruption to the patient, and also demand dedicated nursing time and resources.

Furthermore, to function correctly, the adhesive membrane applied over the foam wound structures must form an airtight seal with the skin. Obtaining such a seal can be difficult, particularly in body regions where the surrounding skin is tortuous, and/or mucosal and/or moist.

Furthermore, prolonged wearing of wet dressings can cause further breakdown and maceration of the surrounding skin thereby increasing the wound size. This can cause further discomfort to the patient, and the exudate can often be offensive in odor and color causing further embarrassment to the patient. This may, in turn, require more numerous dressing changes and re-padding throughout the day, which is disruptive to the patient and costly both in terms of nursing time and resources.

Furthermore, since the membrane and the material of the foam structures are both in direct contact with tissue, tissue reactions can occur.

There remains a need for improved drains, systems, devices, methods that are cost-effective, patient-friendly, and clinician-friendly.

SUMMARY OF THE INVENTION

The invention provides assemblies, systems, and methods that are cost-effective, patient-friendly, and clinician-friendly. The assemblies, systems, and methods convey fluid from an internal wound site or body cavity by applying negative pressure from a source that is outside the internal wound site or body cavity through a wound drain assembly that is placed directly inside the internal wound site or body cavity. Unlike conventional VAC devices, the assemblies, systems, and methods that embody the technical features of the invention are not a treatment modality that is limited to placement on an exterior wound or operational site following trauma or surgery, providing drainage in a reactive and localized fashion. Instead, the assemblies, systems, and methods that embody the technical features of the invention make possible a treatment modality that is sized and configured for placement directly inside an internal wound site or body cavity at the time of surgery, to provide direct and immediate drainage of any entire wound site in a proactive fashion.

One aspect of the invention provides a wound drain assembly comprising a housing enclosing an open interior. The housing is sized and configured for placement directly within an interior wound site or body cavity. Perforations in the housing communicate with the open interior. A foam sponge material is carried within the open interior. The foam sponge material absorbs fluid residing in the interior wound site or body cavity. Tubing is coupled to the housing in communication with the open interior of the housing. The tubing extends from within the interior wound site to outside the interior wound site or body cavity. The tubing outside the interior wound site or body cavity is sized and configured to be coupled to a source of negative pressure outside the body cavity. The negative pressure conveys through the tubing fluid that is absorbed by the foam sponge material inside the internal wound site or body cavity.

Another aspect of the invention provides a wound drain system comprising a wound drain assembly as just described, which is coupled to a source of negative pressure outside the body cavity.

Another aspect of the invention provides a wound drain assembly comprising a wound drainage structure comprising a material capable of being absorbed by the body. The wound drainage structure is sized and configured to absorb fluid in an interior wound site or body cavity. According to this aspect of the invention, tubing is releasably coupled to the wound drainage structure. The tubing extends outside the interior wound site or body cavity to be coupled to a source of negative pressure outside the body cavity to convey fluid absorbed by the material from the internal wound site or body cavity. After conveying the desired volume of fluid from the body, the tubing can be disconnected from the wound drainage structure, to allow the wound drainage structure to be absorbed by the body.

Other aspects of the invention provide methods that provide the wound drain assembly or system as above described and that operate the assembly or system to convey fluid from an interior wound site or body cavity.

The assembly, system, and/or method apply a vacuum of significant pressure internally and directly in a wound area or body cavity for enhanced wound healing benefits. By applying a vacuum of significant consistent pressure internally and directly in the wound area or body cavity, the assembly, system, and/or method reduce the "dead-space" or open area inside the wound or cavity, and thereby aid in decreasing tissue edema and swelling of the overlying and underlying tissue. The assembly, system, and/or method increase the nature and extent of wound drainage, promote tissue adherence and closure of wounds, and thus decrease seroma formation and promote primary wound healing. The assembly, system, and/or method thereby decrease the costly and increased patient morbidity caused by seroma formation and the resultant delay in primary wound healing or need for additional surgical procedures or drainage.

BRIEF DESCRIPTION OF THE DRAWINGS

FIG. 4 is an anatomic side section view of a human abdomen, like that shown in FIG. 1, but showing a drain system that embodies features of the invention, comprising an internally placed wound drain assembly coupled to an external source of negative pressure.

FIG. 5 is an anatomic, somewhat diagrammatic view of the enhanced drainage area achieved by the drain system shown in FIG. 4.

FIG. 18 shows, in an anatomic view, a system like that shown in FIG. 4, comprising a wound drain assembly coupled to a portable source of negative pressure that can be carried by an individual, but also be fixed or attached to a wall section.

FIGS. 19A, 19B, and 19C show, in an anatomic view, s system like that shown in FIG. 4, comprising an absorbable would drain assembly.

DESCRIPTION OF THE PREFERRED EMBODIMENT

Figure 1:
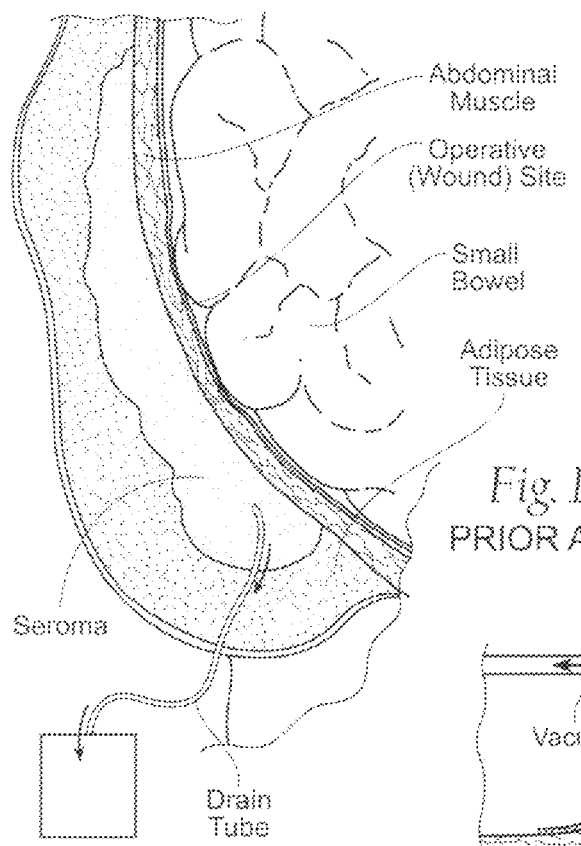
FIG. 1 is an anatomic side section prior art view of a human abdomen showing an interior wound area and a tube that is placed according to conventional techniques to drain fluid from a seroma at the wound site.
Figure 2:
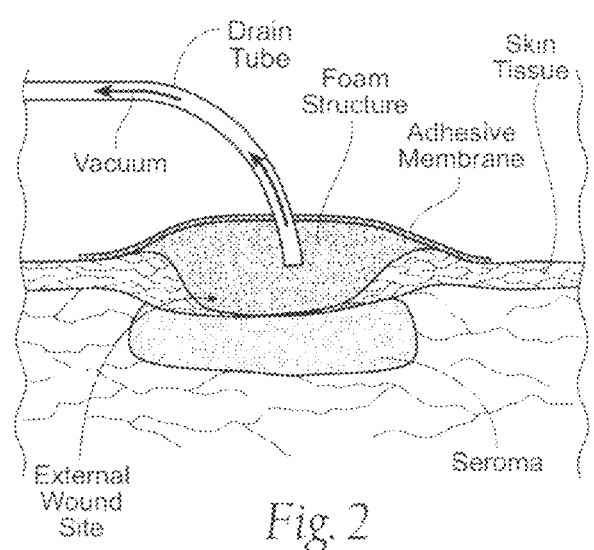
FIG. 2 is an anatomic side section prior art view of an exterior wound area showing an external VAC device placed according to conventional techniques to drain fluid from a seroma only at an external wound site.
Figure 3:
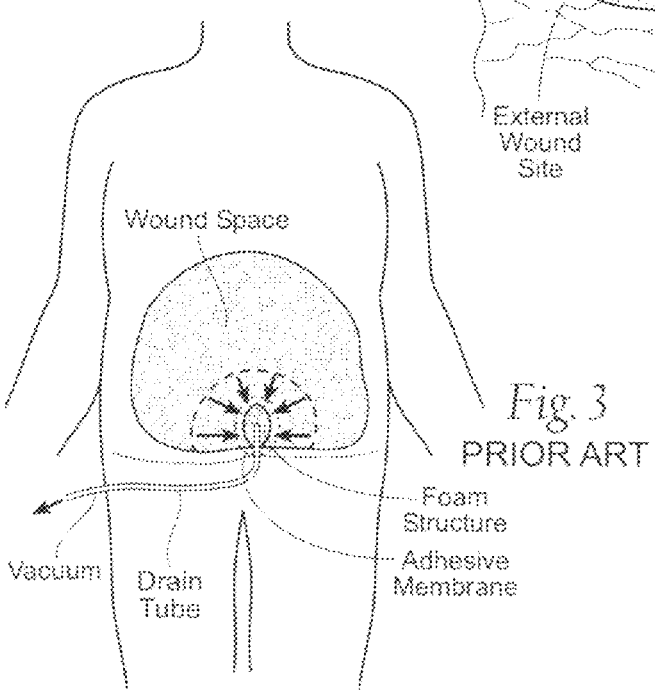
FIG. 3 is an anatomic, somewhat diagrammatic prior art view of the limited drainage area achieved by the external VAC device shown in FIG. 2.

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

FIG. 4 shows a wound drainage system 10 comprising an internal drain assembly 12 that is sized and configured for surgical placement within a wound area W (or body cavity). The wound area W may be anywhere in a human or animal, e.g., within a body cavity, or beneath the skin, or in muscle, or within the soft tissues. As will be described in greater detail later (see FIG. 6), the internal drain assembly 12 includes a housing 18 that encloses a foam sponge component 16. The foam sponge component 16 communicates with the wound area W through one or more apertures 20 formed in the housing 18.

The internal drain assembly 12 is coupled to drain tubing 14, which is desirable flexible. The drain tubing 14 extends outside the wound area W. The drain tubing 14 can extend through a percutaneous incision in the skin overlying any wound area W. Alternatively, the drain tubing 14 can extend through an opening in a skin flap bounding the wound area. The flexible drain tubing 14 includes a terminal end 22 that extends outside the body.

The terminal end 22 desirably includes a quick release connector 24. The connector 24 is sized and configured to be connected to a conventional external negative pressure suction device 26 (such as a V.A.C.® device made by KCI International, or a conventional wall suction or other regulated vacuum device).

In use, the drain tubing 14 is connected to the suction device 26, and the suction device 26 is operated to apply a requisite negative pressure through the internal drain assembly 12. Blood or serous fluid absorbed by and passing through the foam sponge component 16 are drawn by the negative pressure from the wound area W. The drain tubing 14 desirably includes an inline reservoir 30 to collect the withdrawn fluid for disposal.

As FIG. 5 shows, occupying the interior of the wound area W, the internal drain assembly 12 conveys negative pressure throughout the entire open volume of the wound space. The negative pressure applied by the internal drain assembly 12 clears fluid from the entire wound volume. The removal of fluid from the entire wound volume promotes tissue adherence within the wound space, to close the wound space and seal the wound.

As FIGS. 4 and 5 show, the drain tubing 14 desirably includes an inline one-way backflow valve V. The one-way backflow valve V allows fluid to be drawn from the wound volume into the reservoir 30. Upon disconnection of the drain tubing 14 from the external negative pressure suction device 26 (via the connector 24), the one-way backflow valve V prevents air or fluid to flow backward into the wound or body. The one-way backflow valve V keeps the internal drain assembly 12 closed when not connected to the external negative pressure suction device 26.

Figure 6:
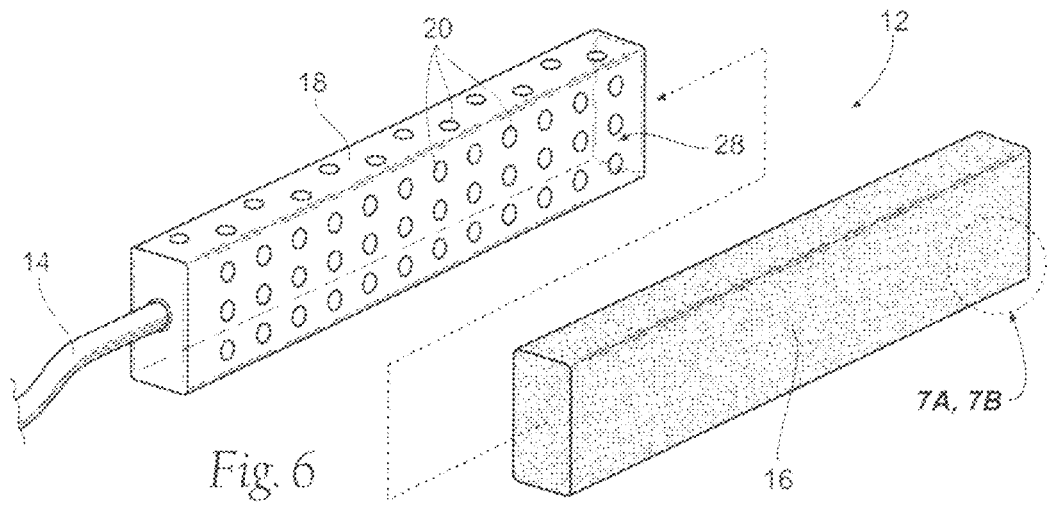
FIG. 6 is a perspective, exploded view of a representative embodiment of a wound drain assembly of the type shown in FIG. 4.
Figure 8:
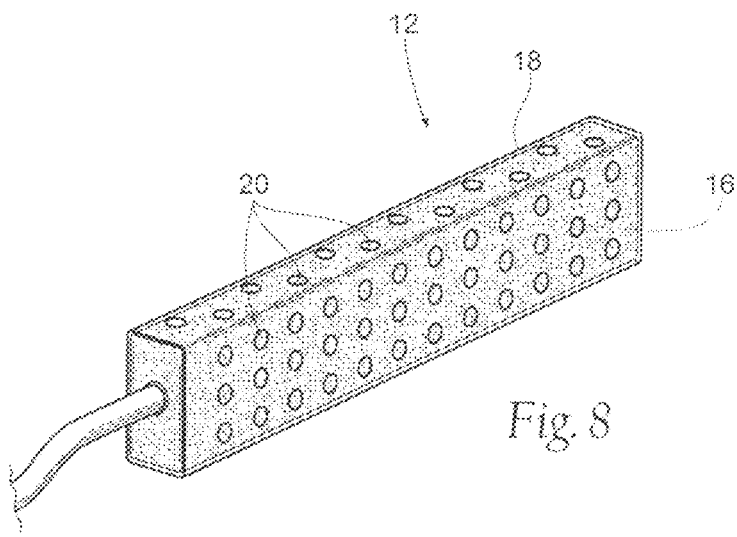
FIG. 8 is a perspective, assembled view of the wound drain assembly shown in FIG. 6.
Figure 9:
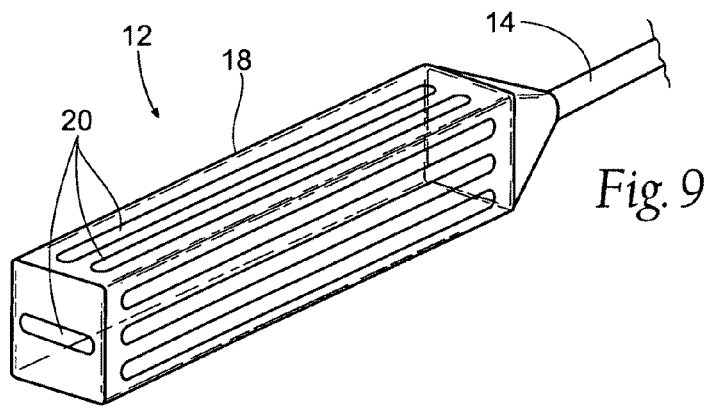
FIGS. 9 to 13 are perspective views of other representative embodiments of a wound drain assembly of the type shown in FIG. 4.
Figure 10:
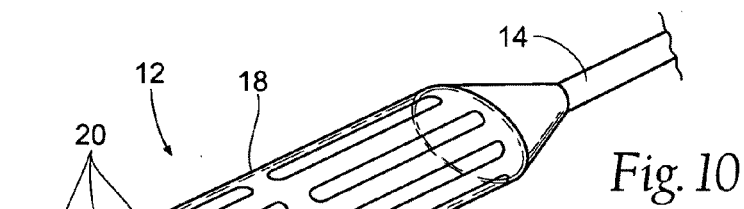
Figure 11:
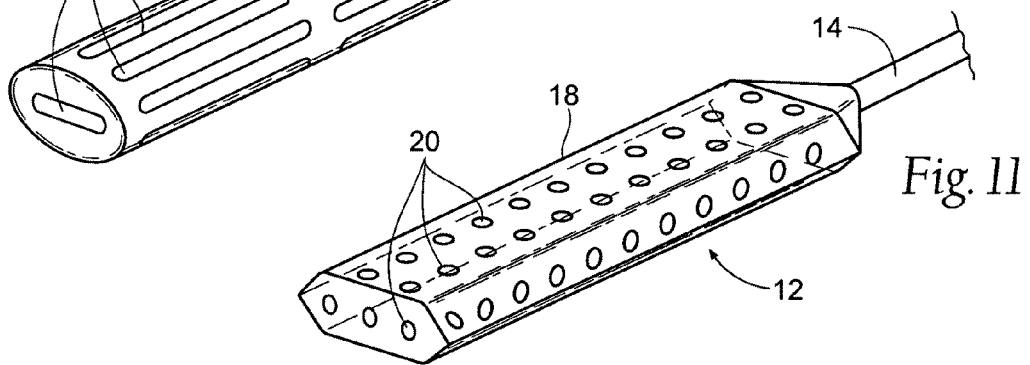
Figure 12:
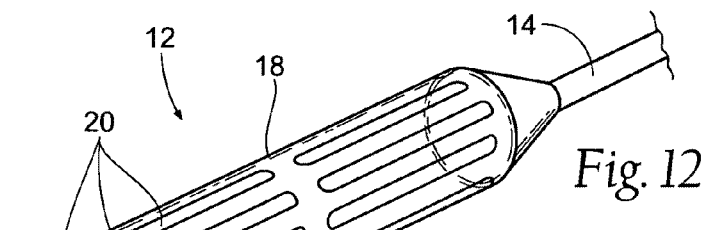
Figure 13:
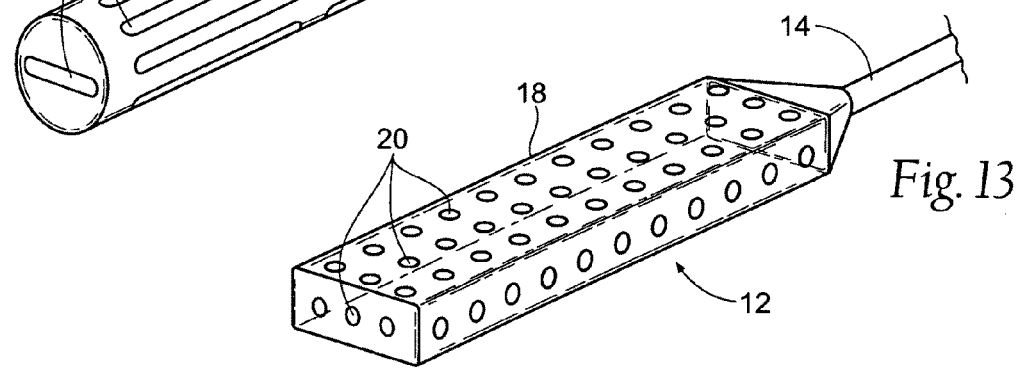

As FIGS. 6 and 8 show, the internal drain assembly 12 comprises a housing 18. The housing 18 is made from an inert, biocompatible material that does not adhere to or activate the body's natural foreign body defense mechanism. The material can comprise, e.g., silicone rubber, polyurethane, or other biocompatible plastics.

The housing 18 can be formed. e.g., by extrusion, molding, or machining. As will be described in greater detail later, the housing 18 can be formed in various shapes and sizes, depending upon the requirements and morphology of the wound site and function and use of the drain. In the configuration shown in FIG. 8, a representative size measures about 5" (length)×about ¾" (width)×about ½" (height).

The housing 18 is formed to include a hollow interior chamber 28, which is enclosed by the side and end walls of the housing 18. The housing 18 is also formed to include one or more through-slots, through-apertures, or through-perforations 20 in the side and/or end walls of the housing 18. The through-slots, through-holes, or through-perforations 20 open the hollow interior chamber 28 to communication with the wound site environment outside the housing 18.

An end of the flexible drain tubing 14 is coupled to the housing 18 and opens into the hollow interior chamber 28. The flexible drain tubing 14 is made of medical grade, inert material. e.g., silicone rubber, polyurethane, or other biocompatible plastics. The tubing is desirably sized and configured to accommodate sufficient fluid flow with a relatively small and tolerable incision size (e.g., about 2-3" in diameter).

Figure 7A:
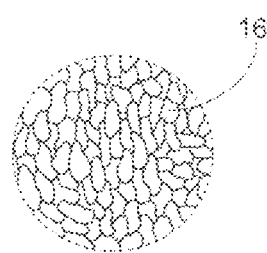
FIGS. 7A and 7B are enlarged views of representative forms of foam sponge material that the wound drain assembly shown in FIG. 6 carries.
Figure 7B:
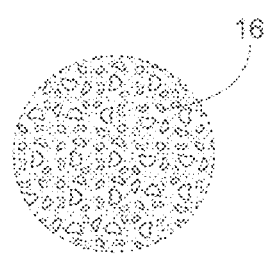

A foam sponge component 16 is housed within the hollow interior chamber 28. The foam sponge component 16 is characterized in that it does not break into particulates in the presence of fluid and pressure. The foam sponge material can comprise, e.g., an open-cell porous structure (see FIG. 7A) or a granulated foam construction (see FIG. 7B). The foam sponge component 16 can be variously constructed from a biocompatible material that does not adhere to or activate the body's natural foreign body defense mechanism, e.g., sponge materials used with conventional VAC devices. As stated later, the foam sponge component 16 can be impregnated with antibacterial products or solutions, or other hormone or natural or manmade stimulating factors that can decrease the chance of infection and/or accelerate wound healing.

In use (as FIGS. 4 and 5 show), the internal drain assembly 12 is placed within an interior of the wound area W (or body cavity). Fluids collecting in the wound or body cavity are absorbed by and pass through the foam sponge component 16 through the perforations 20 in the housing 18. Fluid absorbed by the foam sponge component is siphoned away by the drain tubing 14 when a requisite negative pressure is applied.

The negative pressure can be, e.g., 125 to 200 mmHg, and is desirably about 125 mmHg, below ambient pressure. The amount of negative vacuum pressure can, be regulated in a continuous, discontinuous, or otherwise variable manner, to maximize wound healing and closure and thereby reduce overlying soft tissue edema and swelling. In this way, the system 10 promotes primary wound healing while also decreasing or minimizing seroma formation.

Figure 16:
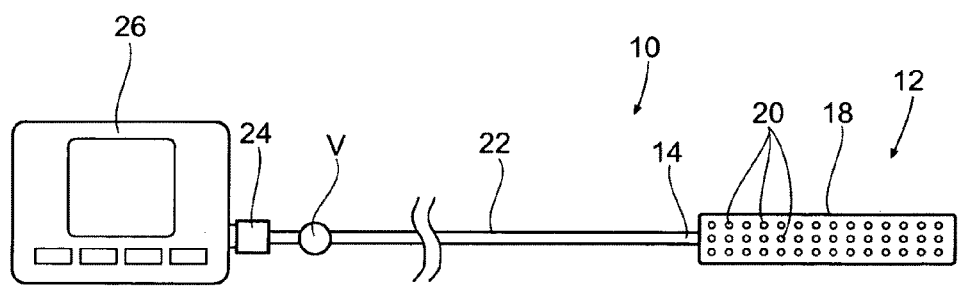
FIGS. 16 and 17 show, respectively, a wound drain assembly of the type shown in FIG. 4 before and during the application of negative pressure.
Figure 17:
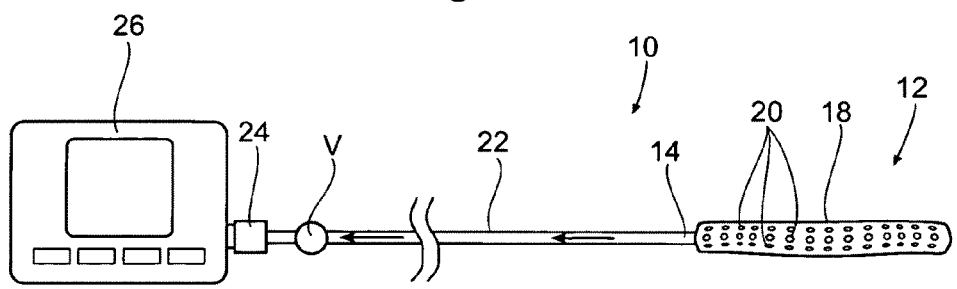

As FIGS. 16 and 17 show, the introduction of negative pressure into the housing 18 can cause the housing 18 to collapse against the foam sponge component 16 (as FIG. 17 shows), while the through-perforations 20 of the housing 18 maintain open paths for fluid to be absorbed by the foam sponge component 16.

The foam sponge component 16 is desirably compressible for easy insertion into and removal from the housing 18 for replacement. The configuration of the housing 18 can also provide a contour that facilitates sliding of the internal drain assembly 12, easing removal from the body.

The foam sponge component 16 may also be impregnated with components such as silver or antibacterials or other growth factors that may decrease infection and promote wound healing.

The foam sponge component may also include other hormone or natural or manmade stimulating factors that can decrease the chance of infection and/or accelerate wound healing.

As FIGS. 9 to 13 show, the housing 18 can be formed in various dimensions, shapes, and sizes, and the foam sponge component 16 cut to corresponding dimensions, shapes, and sizes. These dimensions, shapes, and sizes can comprise, e.g., square (FIG. 9); oval (FIG. 10); hexagonal (FIG. 11); round (FIG. 12); or rectangular (FIG. 13); or any linear or curvilinear shape or combinations thereof. The ends of the housing 18 can be tapered or not tapered (as FIGS. 9 to 13 demonstrate). The through-perforations 20 can also be variously shaped and sized (as FIGS. 9 to 13 demonstrate). The through-perforations 20 can also be tapered or not tapered along their axes.

Figure 14:
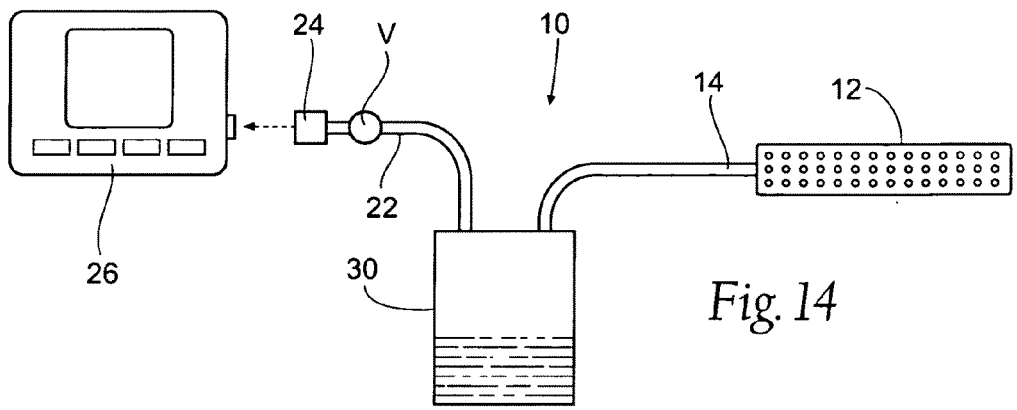
FIGS. 14 and 15 are representative views of various systems of a type shown in FIG. 4.
Figure 15:
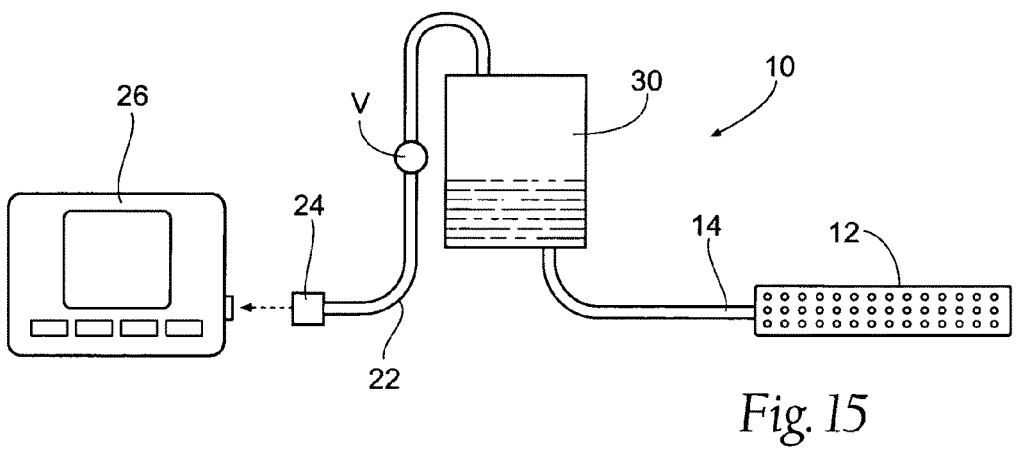

The wound drainage system 10 can be variously configured and assembled. For example, as shown in FIG. 14, the in-line reservoir 30 is intended, in use, to be placed at a gravity position at or below the drain assembly 12 and includes separate fluid inlet and vacuum outlet paths arranged along the top of the reservoir 20, coupled, respectively, to the internal drain assembly 12 and the external negative pressure suction device 26. As FIG. 15 shows, the reservoir 30 is intended, in use, to be placed at a gravity position above the drain assembly 12 and includes an fluid inlet path arranged along the bottom of the reservoir 30 (coupled to the drain assembly 12) and a vacuum outlet port arranged along the top of the reservoir 30 (coupled to the external negative pressure suction device 26).

As FIG. 18, the system 10 may include a battery powered external negative pressure suction device 26' that can be carried by the individual. The system 10 can therefore be operated while the individual ambulates, so that the individual need not be bed-bound during the recovery period.

Figure 19B:
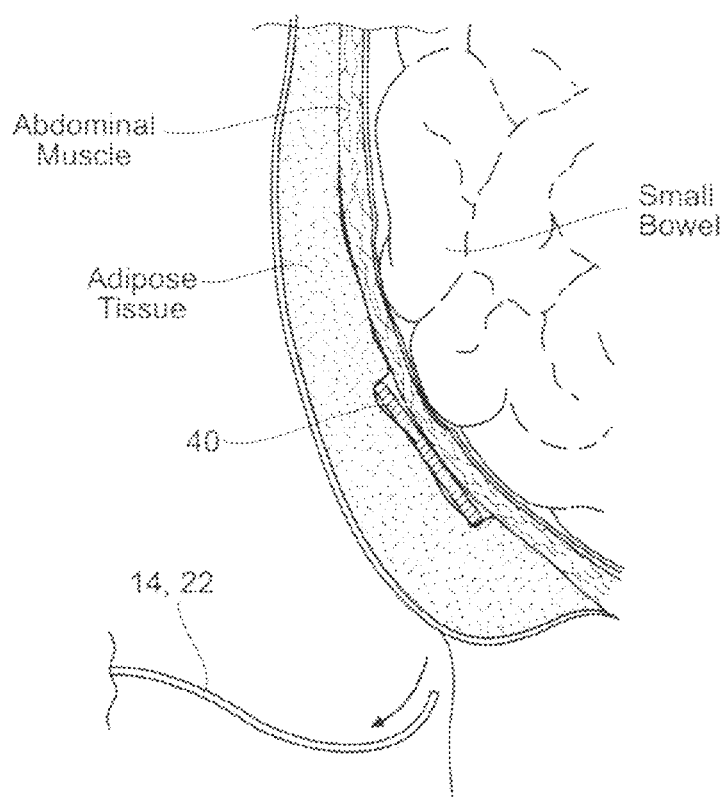
Figure 19C:
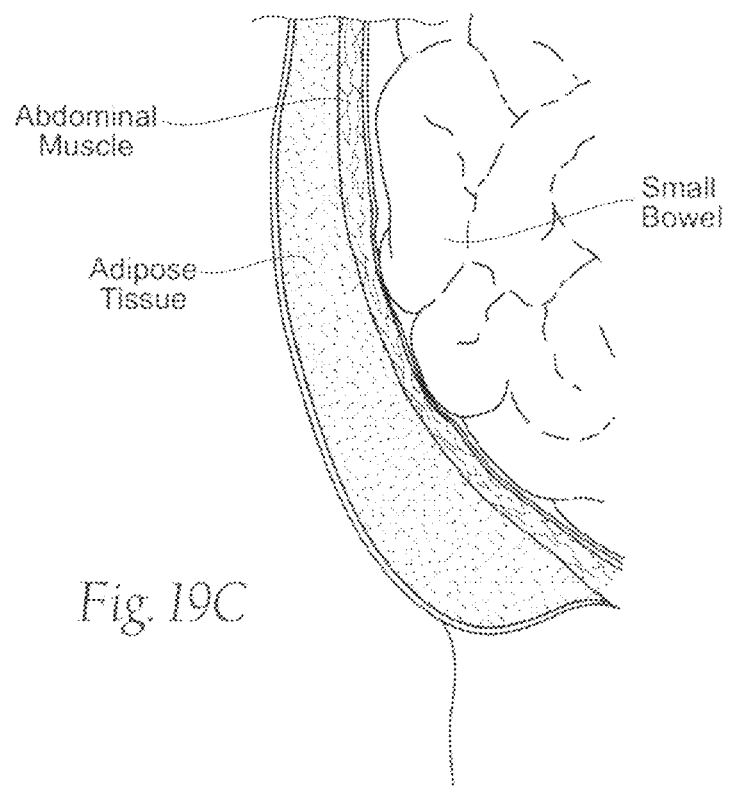

As shown in FIG. 19A, the internal drain assembly 12 can comprise an absorbable mesh structure 40 coupled to the tubing 12. The absorbable mesh structure 40 can be made of sterile material, such as, e.g., Vicryl, moncryl, PDS or other absorbable material that could be woven into a foam-like construct. In this embodiment, when the internal drain assembly 12 has completed its job (see FIG. 19B), the silicone or plastic tubing 14 is detached from mesh structure 40 and removed, leaving the absorbable mesh structure 40 inside the body, to dissolve and absorb just like absorbable suture, as shown in FIG. 19C.

It is believed that applying a vacuum of significant pressure internally and directly in a wound area or body cavity removes chronic edema and leads to increased localized blood flow. It is also believed that the applied forces applied internally and directly in a wound area result in the enhanced formation of tissue adherence. It is further believed that applying a vacuum of significant pressure internally and directly in a wound area or body cavity will accelerate healing by the application of a universal negative force to the entire wound volume, drawing the wound edges together, assisting closure, enhancing wound healing, and decreasing dead space and seroma. Presumed mechanisms responsible for achieving these objectives include: (i) changes in microvascular blood flow dynamic; (ii) changes in interstitial fluid; (iii) removal of wound exudates; (iv) stimulation of growth factors and collagen formation; (iv) reduction in bacterial colonization; (v) mechanical closure of wound by "reverse tissue expansion;" (vi) increasing adherence of the soft tissue and internal wound healing; and (vii) decreasing dead space and seroma formation.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method comprising creating percutaneous access into a wound of an individual defined by an interior dead space having a volume enclosed between interior tissue surfaces consisting of muscle, connective, or skin tissue containing blood vessels that have been separated by surgery or trauma within a body beneath substantially intact skin, and in which extracellular blood and serous fluid escaping from the blood vessels can accumulate to form a seroma, providing a wound closure device comprising a wound drainage structure sized and configured for placement entirely within the interior dead space, the wound drainage structure comprising a perforated housing, the wound closure device comprising tubing coupled to the wound drainage structure, the tubing sized and configured to be coupled to a source of negative pressure outside the body to convey negative pressure for application internally into the interior dead space, placing the wound drainage structure within the interior dead space, extending the tubing from the interior dead space through the percutaneous access to a location outside the body, coupling the tubing to a source of negative pressure outside the body, operating the source of negative pressure to convey negative pressure at a negative pressure at 125 to 200 mmHg below ambient pressure into the wound closure device for application internally into the interior dead space, and in response to the applied negative pressure, conveying extracellular blood and serous fluid from the interior dead space through the perforated housing to draw together the separated interior tissue surfaces to promote adherence of the tissue surfaces, closure of the dead space during a wound healing process.

2. A method according to claim 1 wherein the tubing includes a connector for releasable connection to the source of negative pressure outside the body.

3. A method according to claim 1 further including collecting the extracellular blood and serous fluid in a reservoir communicating with the tubing outside the body.

4. A method according to claim 1 wherein the tubing is flexible.

5. A method according to claim 1 wherein the tubing conveys negative pressure through one or more apertures for application internally into the interior dead space.

6. A method according to claim 1 wherein the wound drainage structure comprises a material communicating with the tubing to take in the extracellular blood serous fluid from the interior dead space.

7. A method according to claim 6 wherein the material does not break into particulates in the presence of fluid and pressure.

8. A method according to claim 6 wherein the material is capable of being absorbed by the body, further including, after drawing together the separated interior tissue surfaces to promote adherence of the tissue surfaces, closure of the dead space, during the wound healing process, separating the tubing from material, removing the tubing from the open interior, and allowing the material to be absorbed by the body.

9. A method according to claim 6 wherein the material comprises an open cell material.

10. A method according to claim 6 wherein the material comprises a foam sponge material.

11. A method according to claim 1 wherein operating the source of negative pressure includes regulating the negative pressure in a continuous manner.

12. A method according to claim 1 wherein operating the source of negative pressure includes regulating the negative pressure in a variable manner.

13. A method according to claim 1 wherein the source of negative pressure is portable.

14. A method according to claim 1 wherein the source of negative pressure can be carried by the individual.

15. A method comprising
creating percutaneous access into a wound of an individual defined by an interior dead space having a volume enclosed between interior tissue surfaces consisting of muscle, connective, or skin tissue containing blood vessels that have been separated by surgery or trauma within a body beneath substantially intact skin, and in which extracellular blood and serous fluid escaping from the blood vessels can accumulate to form a seroma,
providing a portable source of negative pressure that is battery powered and can be carried by the individual,
providing a wound drainage structure comprising tubing having a proximal region sized and configured to be coupled to the portable source of negative pressure outside the body and a distal region having a perforated housing sized and configured to extend from the source of negative pressure through a percutaneous access in the substantially intact skin to a location within the interior dead space to convey negative pressure for application internally into the interior dead space,
coupling the proximal region of the tubing to the portable source of negative pressure outside the body,
placing the distal region of the tubing through a percutaneous access in the substantially intact skin in a location within the interior dead space to convey negative pressure for application internally into the interior dead space,
operating the portable source of negative pressure at a negative pressure at 125 to 200 mmHg below ambient pressure while the individual ambulates and carries the portable source of negative pressure, thereby conveying extracorporeal blood and serous fluid through the perforated housing into the tubing from the interior dead space and draw the separated interior tissue surfaces together to promote adherence of the tissue surfaces and closure of the dead space.

16. A method according to claim 15 wherein the tubing includes a connector for releasable connection to the portable source of negative pressure outside the body.

17. A method according to claim 15 further including collecting the extracellular blood and serous fluid in a reservoir communicating with the tubing outside the body.

18. A method according to claim 15 wherein the tubing is flexible.

19. A method according to claim 15 wherein the tubing conveys negative pressure through one or more apertures for application internally into the interior dead space.

20. A method according to claim 15 wherein the wound drainage structure comprises a material communicating with the tubing to take in the extracellular blood and serous fluid from the interior dead space.

21. A method according to claim 20 wherein the material does not break into particulates in the presence of fluid and pressure.

22. A method according to claim 20 wherein the material is capable of being absorbed by the body, further including, after drawing together the separated interior tissue surfaces to promote adherence of the tissue surfaces, closure of the dead space, during a wound healing process, separating the tubing from material, removing the tubing from the open interior, and allowing the material to be absorbed by the body.

23. A method according to claim 20 wherein the material comprises an open cell material.

24. A method according to claim 20 wherein the material comprises a foam sponge material.

25. A method according to claim 15 wherein operating the source of negative pressure includes regulating the negative pressure in a continuous manner.

26. A method according to claim 15 wherein operating the source of negative pressure includes regulating the negative pressure in a variable manner.

* * * * *